United States Patent [19]
Richeda

[11] Patent Number: 5,971,759
[45] Date of Patent: *Oct. 26, 1999

[54] DENTAL POST AND PIN REPAIR

[76] Inventor: Fred A. Richeda, P.O. Box 57493, Salt Lake City, Utah 84157-0493

[ * ] Notice: This patent is subject to a terminal disclaimer.

[21] Appl. No.: 09/062,563

[22] Filed: Apr. 20, 1998

Related U.S. Application Data

[63] Continuation-in-part of application No. 08/542,916, Oct. 13, 1995, Pat. No. 5,816,815.

[51] Int. Cl.⁶ ...................................................... A61C 5/08
[52] U.S. Cl. .............................................................. 433/220
[58] Field of Search ..................................... 433/220, 221, 433/225

[56] References Cited

U.S. PATENT DOCUMENTS

| | | | |
|---|---|---|---|
| 3,629,943 | 12/1971 | Gindea | 433/220 |
| 3,874,081 | 4/1975 | Franklin et al. | |
| 4,234,309 | 11/1980 | Sellers . | |
| 4,239,489 | 12/1980 | Ellman et al. | 433/220 |
| 4,260,383 | 4/1981 | Weissman . | |
| 4,451,237 | 5/1984 | Filhol . | |
| 4,600,392 | 7/1986 | Weissman . | |
| 4,622,012 | 11/1986 | Smoler | 433/221 |
| 4,824,371 | 4/1989 | Deutsch et al. | 433/189 |
| 4,846,685 | 7/1989 | Martin | 433/221 |
| 4,867,683 | 9/1989 | Meisel . | |
| 5,104,321 | 4/1992 | Filhol | 433/221 |

FOREIGN PATENT DOCUMENTS

| | | |
|---|---|---|
| 3512938 | 10/1986 | Germany . |
| 1498485 | 8/1989 | U.S.S.R. . |
| 9307827 | 4/1993 | WIPO . |

Primary Examiner—Gene Mancene
Assistant Examiner—Pedro Philogene
Attorney, Agent, or Firm—Paul M. Denk

[57] ABSTRACT

A post and pin placed in a radicular or root portion of a tooth as well as in the dentin of fractured or badly broken-down vital teeth to facilitate the distribution of stress throughout the roots and provide structure to support repair parts to restore teeth to a natural shape. Dentistically repair is a method for creating a reservoir space in a tooth to receive a composite resin as well as a stainless steel wire and sleeve components to attach and support a tooth repair part for restorations of a fracture or broken tooth chewing surface. The repair components provide a utilitarian structure of a unique nature.

5 Claims, 3 Drawing Sheets

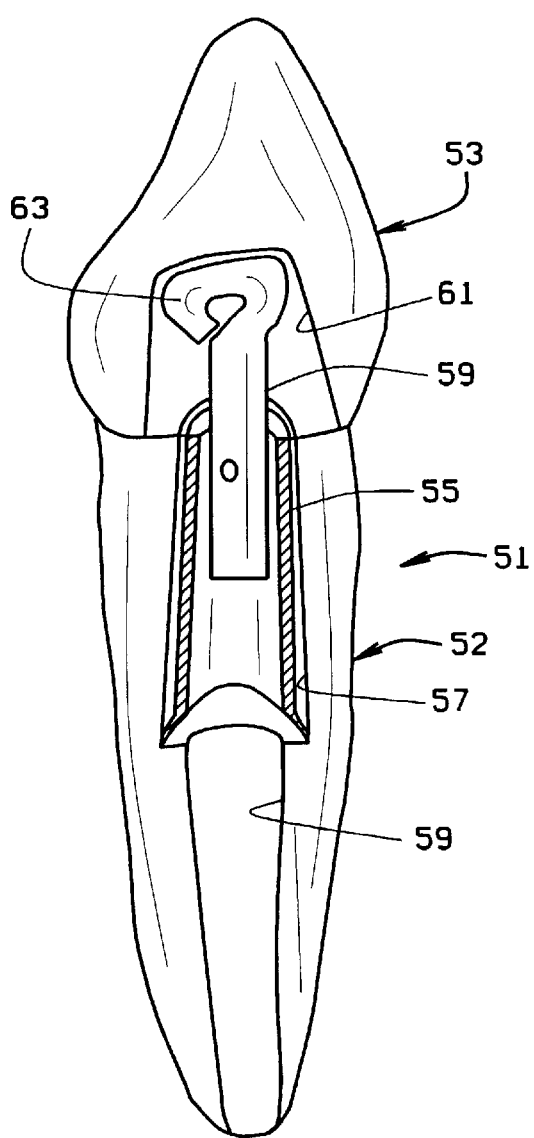
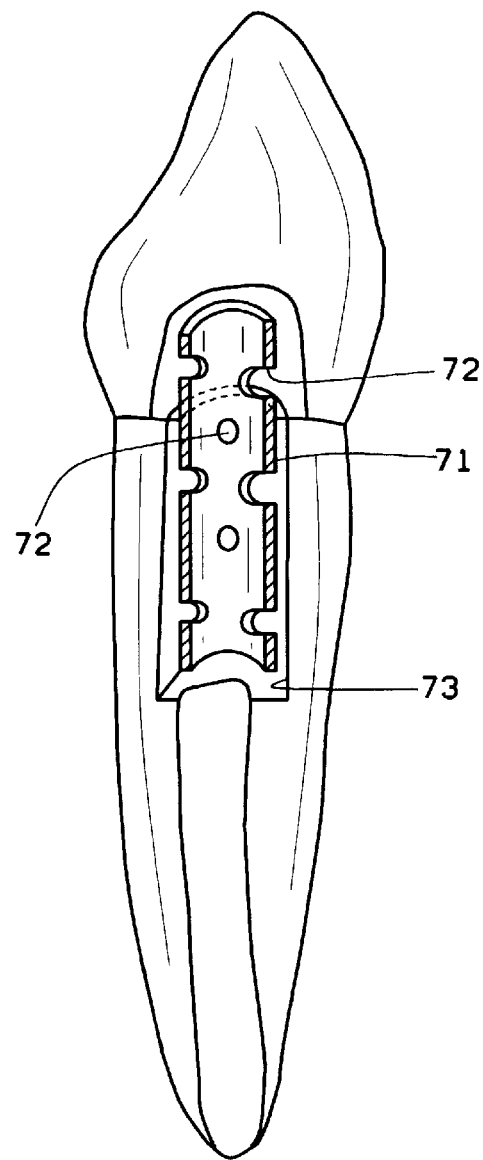
FIG. 5
FIG. 6

DENTAL POST AND PIN REPAIR

CROSS-REFERENCE TO RELATED APPLICATIONS

This is a continuation-in-part of application Ser. No. 08/542,916 filed Oct. 13, 1995, now U.S. Pat. No. 5,816,815, which is incorporated herein by reference.

BACKGROUND OF THE INVENTION

This invention relates to a dental post or sleeve assembly for anchoring dental repair super structures, such as crowns and veneers, onto a tooth, and a method for effecting permanent installation of the pin.

The prior art has presented a wide variety of structures for the repair and reconstruction of broken or mutilated teeth. In this category of dental repair, the reconstruction of a tooth has required an expensive anchoring pin to make the reconstruction successful. Pin anchors must be carefully shaped and located so the reconstruction installation can be reasonably free of stress and can properly align with adjacent teeth. The problem with such approaches for reconstruction of a broken or mutilated tooth becomes impractical because of space limitations and unnatural alignment with adjacent teeth.

In the category of dental pins of the threaded variety, the problem is related to the extreme care needed to be exercised to prevent the entrance of impurities. Furthermore, threaded type pins are small and difficult to handle. Contoured parts fall into this category of dental repair devices. Stress caused by insertion of the threaded pin is the greatest problem.

SUMMARY OF THE INVENTION

An important object of the invention is to provide post or sleeve suitable for applications in the radicular portion of a tooth as well as placement in the dentin of badly mutilated teeth so that the vertical distribution of stress is facilitated in the root whereby proper support is obtained for the reconstruction.

Another object is to employ a sleeve in a prepared hole in a tooth so that composite material when properly in place can develop the required strength for the repair.

A further object of the invention is to provide an anchor wire which is received in the sleeve to facilitate securement of the reconstruction to the root of the tooth, the sleeve and wire being set in a composite material reservoir in the tooth which is shaped to allow for correct placement of the sleeve and wire, and assuring the union of the combination to obtain natural distribution of stress through the root.

A further object is to locate a sleeve within a prepared hole in a tooth, with the sleeve having predesigned apertures provided therethrough, so that composite material when forced into the sleeve, can surround the anchor wire and pin and exude into the space between the sleeve and the tooth aperture so as to provide greatly enhanced strength for support of the pin in place for holding a crown, or bridge structurally and firmly in place.

Still another object is to rely on a wire post that can be shaped and acid-etched so the substantially the full holding area of the wire becomes available.

Other objects of the invention will be disclosed in connection with the best mode of the invention to be disclosed hereinafter.

Briefly stated, a tooth repair is effected by forming a hole or reservoir in the tooth root having an inverted, truncated cone shape. A post or sleeve is received in the tooth reservoir. The sleeve, which preferably has a series of access holes, is retained in the reservoir by a composite which cures to hold the post in the reservoir. The post can either be flush with the top of the tooth and have a pin which extends above the top of the tooth. Alternately, the post itself can extend above the top of the tooth. In either instance, either the pin or the post is received in a reservoir or hole formed in the tooth repair which is to be secured to the tooth. The composite is placed in the tooth repair reservoir to hold the tooth to the pin or post.

BRIEF DESCRIPTION OF THE DRAWINGS

FIG. 5 is a cross-sectional view of a tooth with a modified sleeve and pin arrangement; and FIG. 6 is a cross-sectional view of a tooth showing a second alternative post or sleeve construction.

BRIEF DESCRIPTION OF THE EMBODIMENT

Figure 1:
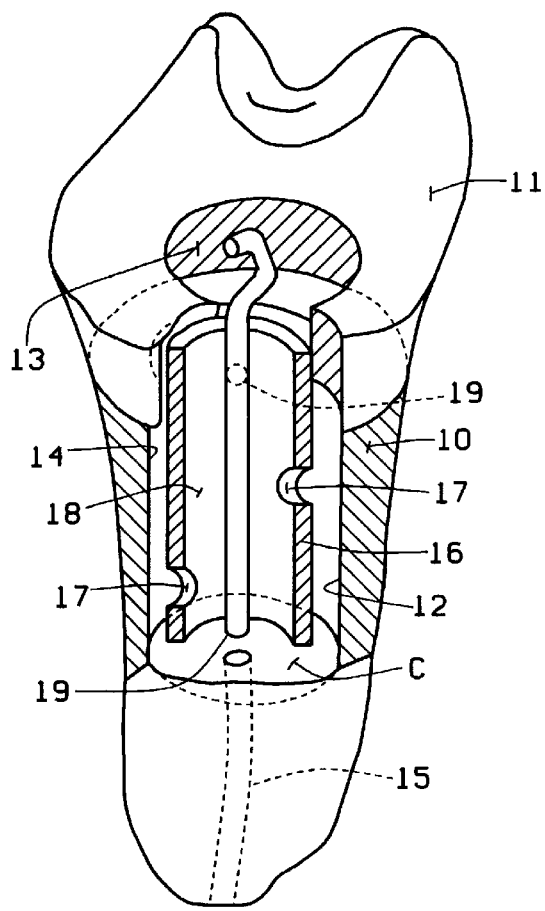
FIG. 1 is a perspective view of a tooth with portions cut away to reveal the components to secure a crown repair on that tooth.

In a dental repair on a tooth 10 needing a crown 11 as a replacement for a natural crown that has been mutilated or otherwise removed, the view of FIG. 1 has been disclosed with the side wall cut away at 12 to better explain the endodontic repair work performed on the tooth 10. As depicted, the top surface 13 of the tooth 10 has been cleaned or ground off and a hole 14 is formed in the central area of the tooth above the root canal 15. The hole 14 receives a metal sleeve 16 which has been provided with access ports 17 distributed around and along the sleeve. The ports 17 open to an annular space 18 defined by the sleeve surrounding a steel wire or pin 19. A composition C is deposited in the space 18 in a timely manner and is placed inside and outside the sleeve 16.

The composition C is a resin having the desired butting or sealing properties which intuitively adheres to the acid etched surface of the sleeve 16 and the wire 19, as well as the dentin wall of the hole 14. The sleeve 16 and wire 19 are fully etched by the acid prior to being placed in the tooth hole 14. The acid etch is generally phosphoric acid, and the resin composition is an oligomer of which the most common are Bis-GMA, urethane-diacrylates, and modified Bis-GMA without the hydroxy groups. Such compositions can be obtained from Western Dental Specialties, of San Diego, Calif. The compositions are cured either with chemical activation or by light. It is important that the compositions have a flow characteristic that readily wets the surfaces of the dentine, sleeve 16 and wire post 19, and can migrate under pressure, through the ports or apertures 17 to completely envelop the sleeve 16.

Figure 2:
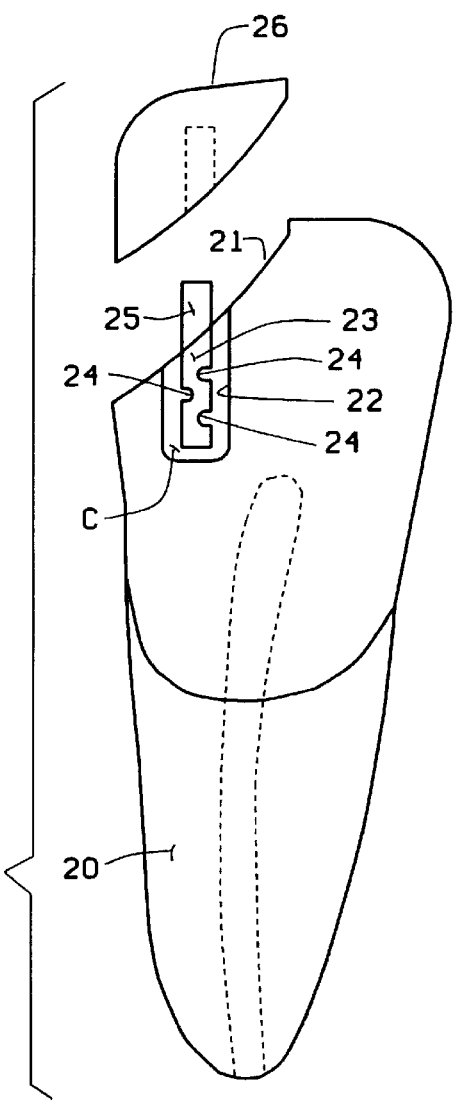
FIG. 2 is a repair of a tooth having a wire or pin implanted to hold a repair thereto.

FIG. 2 is a view of a tooth 20 that needs to be repaired by restoration of a surface or edge fracture 21. In this situation the fracture at 21 has exposed a small part of the tooth 20. The exposed surface is prepared with a shallow hole 22 for the reception of a post 23 formed with side indentations 24 which are positioned in the hole 22. A composition C, as before defined, is placed in the hole 22 so all surfaces of the hole 22 and the post 23 are wetted. Once the post 23 has been set in place, the exposed end 25 of the post is ready to receive the replacement element 26 to repair the fracture and restore the tooth to its natural shape.

Figure 3:
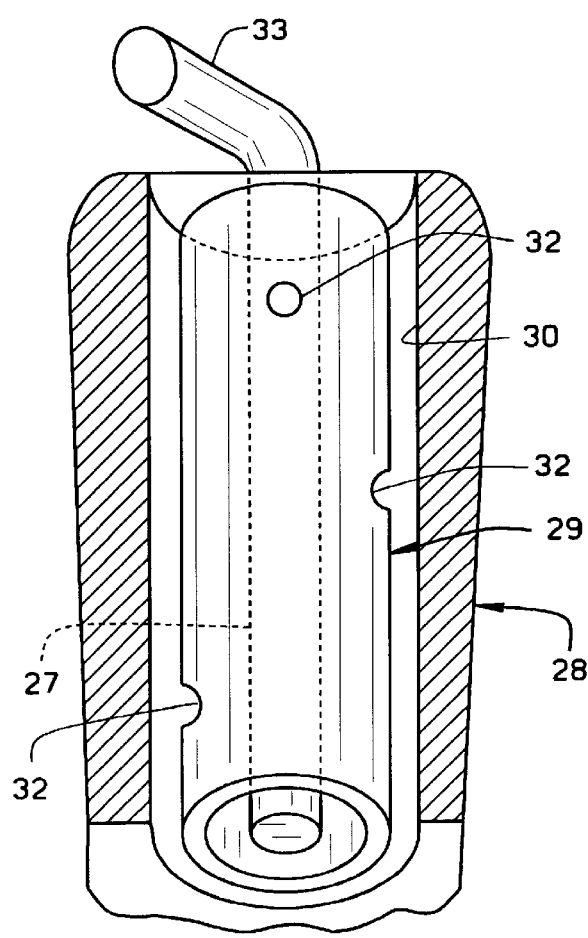
FIG. 3 is a schematic view of a wire or pin implanted post.

FIG. 3 is a schematic view in section of a wire post 27 implanted in a tooth 28 by the combination of a metal sleeve 29 set in a hole 30 in the tooth dentin which makes up the hard calcareous tissue of the tooth 28. The sleeve 29 is formed with apertures 32 distributed around and along the sleeve 29 to receive a composite (not shown) which engages around and inside the sleeve 29. The view of this sketch illustrates that the exposed end portion 33 can be bent, or may be shaped as desired.

In the formation of these sleeves, and the arrangement of their apertures 32, or 17 as shown in FIG. 1, preferably three apertures are arranged along the length of the sleeve. The apertures are located approximately 120° apart and approximately 2 mm apart, in height, away from each other. The initial or upper aperture, as shown in FIG. 3, is arranged approximately 1 mm below the top of the sleeve 29.

Figure 4:
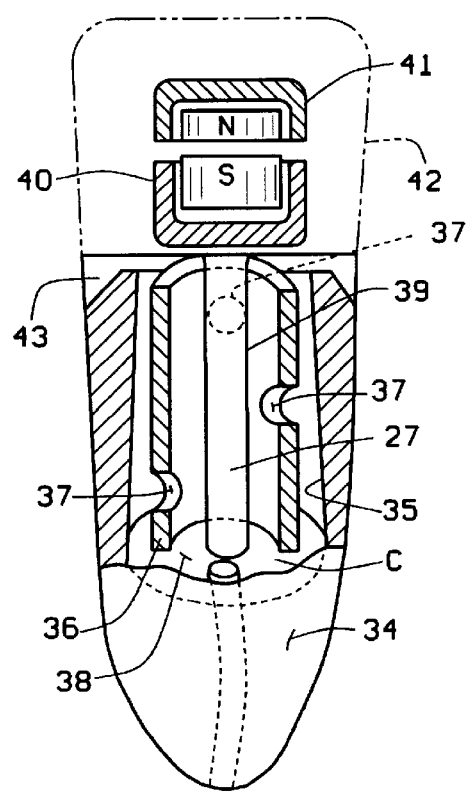
FIG. 4 is a tooth repair utilizing a wire post or pin combined with a magnetic steel device.

FIG. 4 is a special example of a tooth repair in which a magnet receptacle for overdentures in an application that revolutionizes the use of magnets for stabilization of overdentures, or bridgework. The tooth 34 in this case has a hole 35 to receive a sleeve 36 formed with apertures 37 to place the inner and outer sleeve surfaces of the sleeve in communication with each other to receive a composite (not shown) in space 38 to thoroughly seal in the sleeve 36 and metal post 27. The technique for placing the magnetic receptacle 40 is similar to the placing of a post 19 or 23 so the receptacle 40 is properly aligned with other teeth. The denture element 41 is placed in the denture 42 on the underside and luted or sealed in. The magnetic pole pieces N and S are placed in the receptacles 40 and 41 so the denture 42 can be luted to the body of the tooth 34. Extra portions of lute may be required. The ease with which magnetic means can be placed, along with its great retentive poser, distinguishes this treatment.

The tooth 34, which in this case is endodontically treated, has a coping 43 constructed to cover the top of the tooth. A hole 35 is drilled through the top of the coping and into the root to a predetermined depth. The hole 35 receives a sleeve 36 formed with apertures 37 to place the inner and outer sleeve surfaces of the sleeve in communication with each other to receive a composite (not shown) in space 38 to thoroughly seal the sleeve 36 and metal post 27.

FIG. 5 shows a tooth 51 having a root 52 and a crown 53. The root 52 has been prepared for receipt of a hollow sleeve 55 by forming a hole 57 in the root canal 59 of the tooth. The hole 57 is generally in the shape of an inverted, truncated cone. This is performed using a straight fissure bur is initially used to develop a straight channel in the root canal to a depth of approximately one-half of the length of the total root. Next, an inverted cone-shaped bur is used to create an undercut to give the channel its inverted cone shape.

The hole 57 is filled with the composition, as described above, to hold the sleeve 55 and its associated pin 59 in the root of the tooth. As shown, the post or sleeve 57 extends substantially the full length of the hole 57, and a top of the sleeve is generally flush with the top of the root. The pin 59 is received in the sleeve and is held in the sleeve by the composition. The pin 59 extends up beyond the end of the sleeve to be received in a hole 61 formed in the tooth repair or crown 53. The hole 61 is also filled with the composition. The composition bonds to the etched pin 59 and to the crown 53 to hold the crown to the root. The pin 59 is shown to have a head or hook 63 which further enhances the attachment of the crown to the root.

Importantly, the undercut of the hole 57 will provide a mechanical impediment to the dislodgment of the post. This dislodgment of the post is also further impeded by the composite-wall to wall linkage (i.e., the bonding of the composite to the wall of the hole 57 and to the post 55).

A further embodiment is shown in FIG. 6. In this embodiment, the post 71 is substantially similar to the posts of FIGS. 1–5, and includes a plurality of access ports 72. The post is situated in a hole 73 which is formed substantially the same way as the hole 57 of FIG. 5. The post 71, as seen, extends up out of the tooth root, to extend into the hole formed in the crown of the tooth. This embodiment thus eliminates the need for the separate pin to hold the crown to the root.

Throughout the foregoing description, it is to be understood that stainless steel must be employed wherever metal is referred to. The luting or sealing composition is set forth as being the most desirable. The stainless steel wire is preferred as it restores fractured teeth that are stress free. The formation of holes can be easily accomplished with twist drills, and the pin can be adjusted by snipping as required, using wire cutters, and the exposed end that is exposed can be adjusted with pliers. Proper wetting contact with the composition C can be obtained with acid etching or chemically curved composite placed on the wire. The final step is light curving of the composite C.

Variations or modifications to the disclosed subject matter of the invention may occur to those skilled in the art. Such variations or modifications are intended to be included within the scope of the defined invention, and encompassed within the claims of any patent issuing hereon.

Having thus described the invention, what is claimed and desired to be secured by Letters Patent is:

1. A method for effecting the repair of a fractured tooth wherein a fractured part of the tooth has separated from the tooth itself, the method comprising:

forming a reservoir space at the location of the tooth fracture at the location of repair, forming a reservoir space in the tooth repair;

introducing a composite resin into the reservoir space of the tooth;

locating a sleeve in the reservoir space to be wetted by the composite resin;

setting the fractured part of the tooth into position on the sleeve to match the natural tooth; and curing the composite resin to secure the tooth repair fractured part to the sleeve and to hold the tooth repair onto the natural tooth.

2. The method set forth in claim 1 wherein a series of holes are formed in the sleeve to provide for locating of the composite resin therein.

3. The method of claim 1 wherein the sleeve extends into the reservoir of the tooth repair.

4. The method of claim 2 wherein a pin is inserted into the sleeve, the pin extending into the reservoir of the tooth repair.

5. The method of claim 1 wherein the reservoir of the tooth is in the shape of an inverted truncated cone.

* * * * *